US009899185B1

(12) United States Patent
Shemesh et al.

(10) Patent No.: US 9,899,185 B1
(45) Date of Patent: Feb. 20, 2018

(54) RESOLVING AMBIGUITIES IN AN ENERGY SPECTRUM

(71) Applicant: APPLIED MATERIALS ISRAEL LTD., Rehovot (IL)

(72) Inventors: Dror Shemesh, Hod Hasharon (IL); Mor Baram, Ness Ziona (IL)

(73) Assignee: APPLIED MATERIALS ISRAEL LTD., Rehovot (IL)

( * ) Notice: Subject to any disclaimer, the term of this patent is extended or adjusted under 35 U.S.C. 154(b) by 0 days.

(21) Appl. No.: 15/134,329

(22) Filed: Apr. 20, 2016

Related U.S. Application Data

(60) Provisional application No. 62/150,509, filed on Apr. 21, 2015.

(51) Int. Cl.
*H01J 37/244* (2006.01)
*H01J 37/28* (2006.01)
*H01J 37/26* (2006.01)

(52) U.S. Cl.
CPC .......... *H01J 37/261* (2013.01); *H01J 37/244* (2013.01); *H01J 37/28* (2013.01)

(58) Field of Classification Search
None
See application file for complete search history.

(56) References Cited

U.S. PATENT DOCUMENTS

| 5,357,110 | A | * | 10/1994 | Statham | G01N 23/223 250/307 |
| 6,996,492 | B1 | * | 2/2006 | Testoni | G01N 23/2252 378/137 |
| 7,220,964 | B1 | * | 5/2007 | Gao | G01B 15/02 250/288 |
| 8,346,521 | B2 | * | 1/2013 | Statham | G01N 23/2252 378/45 |
| 2002/0161534 | A1 | * | 10/2002 | Adler | G01N 21/956 702/35 |
| 2006/0291619 | A1 | * | 12/2006 | Statham | G01N 23/22 378/45 |
| 2008/0035843 | A1 | * | 2/2008 | Hatano | H01J 37/244 250/288 |
| 2011/0129066 | A1 | * | 6/2011 | Statham | G01N 23/2252 378/88 |

* cited by examiner

*Primary Examiner* — Michael Logie
(74) *Attorney, Agent, or Firm* — Kilpatrick Townsend & Stockton LLP (57) ABSTRACT

A system, computer readable medium and a method for material analysis, the method may include (i) receiving or generating (a) an estimated composition of a microscopic element; wherein the estimated composition is responsive to an energy spectrum of, at least, the microscopic element; wherein the energy spectrum is obtained by an energy dispersive X-ray (EDX) detector; additional information related to, at least, the microscopic element, wherein the additional information is not obtained by the energy dispersive X-ray detector; and (ii) resolving an ambiguity in the estimated composition in response to the additional information, wherein the ambiguity occurs when the energy spectrum comprises a predefined energy peak that is attributed to a predefined material of ambiguous EDX composition determination.

20 Claims, 7 Drawing Sheets

```
┌─────────────────────────────────┐     ┌─────────────────────────────────┐
│ Receiving or generating an      │     │                                 │
│ estimated composition of a      │     │ Receiving or generating         │
│ microscopic element.            │     │ additional information that is  │
│ The the estimated composition is│     │ not obtained by the energy      │
│ responsive to an energy spectrum│     │ dispersive X-ray detector. The  │
│ of, at least, the microscopic   │     │ additional information is       │
│ element. The energy spectrum is │     │ related to the microscopic      │
│ obtained by an energy dispersive│     │ element. 212                    │
│ X-ray (EDX) detector. 211       │     │                                 │
└─────────────────────────────────┘     └─────────────────────────────────┘
```

Resolving an ambiguity in the estimated composition in response to the additional information – is such an ambiguity exists. The ambiguity occurs when the energy spectrum comprises a predefined energy peak that is attributed to a predefined material of ambiguous EDX composition determination. 220

Resolving of the ambiguity by selecting a selected material of ambiguous EDX composition determination out of a group of materials of ambiguous EDX composition determination. 222

Responding to the resolving of the ambiguity. 230

FIG. 3

RESOLVING AMBIGUITIES IN AN ENERGY SPECTRUM

CROSS-REFERENCES TO RELATED APPLICATIONS

This application claims the benefit of U.S. Provisional Application No. 62/150,509, filed on Apr. 21, 2015. The disclosure of which is hereby incorporated by reference in its entirety for all purposes.

BACKGROUND OF THE DISCLOSURE

An energy dispersion x-ray detector (EDX) may be used for determining a composition of a microscopic element. An energy dispersion x-ray detector collects x-ray photons emitted as a result of an illumination of the microscopic element and generates an energy spectrum. Energy spectrum means any type of information about energy levels at different wavelengths or frequencies along the spectrum. For example—the energy spectrum can be a histogram that displays the number of X-ray counts for each x-ray energy level. Measuring X ray energies may help to characterize the element from which an x-ray photon was emitted.

Prior art energy dispersion x-ray (EDX) detectors have a limited energy resolution and may be incapable of differentiating between materials (referred to as "materials of ambiguous EDX composition determination") that have energy peaks that differ from each other by an energy difference that is smaller than the energy resolution of the energy dispersion x-ray detector.

For example, Iron (Fe) and Fluorine (F) form a group of materials of ambiguous EDX composition determination. Iron has a characteristic energy peak at 709 eV ("L line"), and Fluorine has a characteristic energy peak at 677 eV. The difference between these energy peaks is 32 eV. An energy dispersive x-ray detector that has an energy resolution of 70 eV cannot distinguish between Iron and Fluorine.

An energy spectrum generated by an energy dispersion x-ray is analyzed by searching for energy peaks that correspond to characteristic energy levels of different materials. The outcome of the analysis is an estimate of the composition of the microscopic element. The estimate of the composition of the microscopic element may be inaccurate when the energy spectrum includes a peak that is attributed to an material of ambiguous EDX composition determination.

Nowadays, EDX is limited and cannot characterize elements that have overlapping x ray peaks. Different techniques can be used, such as wavelength dispersive x-ray spectrometer (WDS), Auger spectrometer and micro-calorimeter. However, the above are either slow or more complicated to integrate onto an in-line platform in the analysis industry.

There is a growing need to improve the accuracy of composition analysis that is based upon an energy spectrum generated by the energy dispersive x-ray detector.

SUMMARY OF THE DISCLOSURE

According to an embodiment of the disclosure there may be provided a system that may include a hardware processor (processor) that may be configured to receive or generate (i) an estimated composition of a microscopic element; wherein the estimated composition may be responsive to an energy spectrum of, at least, the microscopic element; wherein the energy spectrum may be obtained by an energy dispersive X-ray detector; and (ii) additional information related to, at least, the microscopic element, wherein the additional information may be not obtained by the energy dispersive X-ray detector; and resolve an ambiguity in the estimated composition in response to the additional information, wherein the ambiguity occurs when the energy spectrum may include a predefined energy peak that may be attributed to a predefined material of ambiguous EDX composition determination.

According to an embodiment of the disclosure there may be provided a method for material analysis, the method may include (i) receiving or generating (a) an estimated composition of a microscopic element; wherein the estimated composition may be responsive to an energy spectrum of, at least, the microscopic element; wherein the energy spectrum may be obtained by an energy dispersive X-ray (EDX) detector; (b) additional information related to, at least, the microscopic element, wherein the additional information may be not obtained by the energy dispersive X-ray detector; and (ii) resolving an ambiguity in the estimated composition in response to the additional information, wherein the ambiguity occurs when the energy spectrum may include a predefined energy peak that may be attributed to a predefined material of ambiguous EDX composition determination.

The predefined material of ambiguous EDX composition determination belongs to a group of materials of ambiguous EDX composition determination, wherein the resolving of the ambiguity may include selecting a selected material of ambiguous EDX composition determination out of the group of materials of ambiguous EDX composition determination.

The additional information may be indicative of an expected composition of the microscopic element; wherein the selecting of the selected material of ambiguous EDX composition determination may be responsive to the expected composition of the microscopic element.

The microscopic element may be a defect and wherein the additional information may be indicative of a class of the defect, wherein the selecting of the selected material of ambiguous EDX composition determination may be responsive to the class of the defect.

The additional information may include (a) coordinates of the microscopic element within an imaginary plane, and (b) a mapping between the coordinates of the microscopic element within the imaginary plane and an expected composition of the microscopic element; wherein the selecting of the selected material of ambiguous EDX composition determination may be responsive to the mapping and to the coordinates of the microscopic element within the imaginary plane.

The additional information may include (i) coordinates of the microscopic element within an imaginary plane, (ii) a first mapping between the coordinates of the microscopic element within the imaginary plane and a height of the microscopic element, and (ii) a second mapping between the height of the microscopic element and an expected composition of the microscopic element; and wherein the selecting of the selected material of ambiguous EDX composition determination may be responsive to the first mapping, to the second mapping and to the coordinates of the microscopic element within the imaginary plane.

The additional information may be design information indicative of locations of different layers of a substrate and of compositions of the different layers of the substrate; wherein the microscopic element may be either included in the substrate may be located above the substrate.

The additional information may be obtained by processing at least one secondary electron image of a region that may include the microscopic element.

The additional information may be obtained by processing at least one backscattered electron image of a region that may include the microscopic element.

The additional information may be obtained by processing at least one backscattered electron image and at least one secondary electron image of a region that may include the microscopic element.

The additional information may be obtained by comparing between (a) an attribute of a backscattered electron image of a region that may include the microscopic element; and (b) an attribute of a secondary electron image of the region.

The attribute of the secondary electron image may be a relationship between pixels of the microscopic element and pixels of a background area of the region.

The relationship may be a contrast between the pixels of the microscopic element and the pixels of the background area.

The additional information may include a relationship, in an image of a region, between pixels of the microscopic element and pixels of a background area; wherein the region may include the microscopic element and the background area; wherein the image may be a secondary electron image of the region or a backscattered electron image of the region.

The relationship may be a contrast between the pixels of the microscopic element and the pixels of the background area.

According to an embodiment of the disclosure there may be provided a non-transitory computer readable medium that may store instructions that once executed by a computer cause the computer to receive or generate (i) an estimated composition of a microscopic element; wherein the estimated composition may be responsive to an energy spectrum of, at least, the microscopic element; wherein the energy spectrum may be obtained by an energy dispersive X-ray detector; and (ii) additional information related to, at least, the microscopic element, wherein the additional information may be not obtained by the energy dispersive X-ray detector; and resolve an ambiguity in the estimated composition in response to the additional information, wherein the ambiguity occurs when the energy spectrum may include a predefined energy peak that may be attributed to a predefined56 material of ambiguous EDX composition determination.

BRIEF DESCRIPTION OF THE DRAWINGS

The subject matter regarded as the disclosure is particularly pointed out and distinctly claimed in the concluding portion of the specification. The disclosure, however, both as to organization and method of operation, together with substrates, features, and advantages thereof, may best be understood by reference to the following detailed description when read with the accompanying drawings in which:

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION

In the following detailed description, numerous specific details are set forth in order to provide a thorough understanding of the disclosure. However, it will be understood by those skilled in the art that the present disclosure may be practiced without these specific details. In other instances, well-known methods, procedures, and components have not been described in detail so as not to obscure the present disclosure.

Because the illustrated embodiments of the present disclosure may for the most part, be implemented using electronic components and circuits known to those skilled in the art, details will not be explained in any greater extent than that considered necessary as illustrated above, for the understanding and appreciation of the underlying concepts of the present disclosure and in order not to obfuscate or distract from the teachings of the present disclosure.

Any reference in the specification to a method should be applied mutatis mutandis to a system capable of executing the method and should be applied mutatis mutandis to a non-transitory computer readable medium that stores instructions that once executed by a computer result in the execution of the method.

Any reference in the specification to a system should be applied mutatis mutandis to a method that may be executed by the system and should be applied mutatis mutandis to a non-transitory computer readable medium that stores instructions that may be executed by the system.

Any reference in the specification to a non-transitory computer readable medium should be applied mutatis mutandis to a system capable of executing the instructions stored in the non-transitory computer readable medium and should be applied mutatis mutandis to method that may be executed by a computer that reads the instructions stored in the non-transitory computer readable medium.

FIGS. 1A-1E illustrate systems 10 according to various embodiment of the disclosure.

Figure 1A:
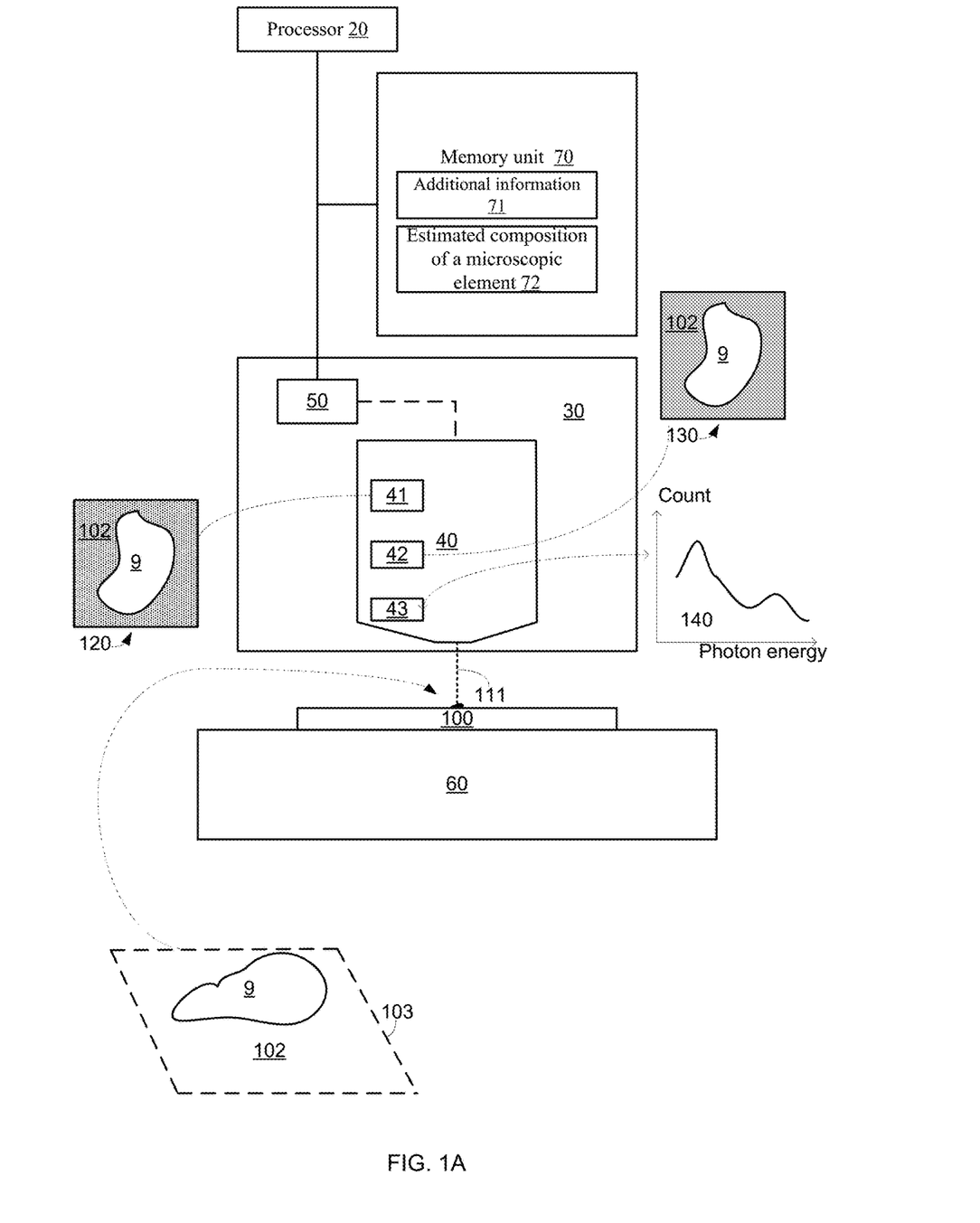
FIG. 1A illustrates a system and a substrate according to an embodiment of the disclosure.

FIG. 1A illustrates system 10 as being a charged particles imager such as but not limited to a scanning electron microscope (SEM) or an electron beam inspection system.

System 10 includes an image obtaining module 30, processor 20, a memory unit 70 and a mechanical stage 60 for supporting and moving a substrate 100.

Substrate 100 may be a wafer, a mask, or a die, or any other object that can be imaged using charged particles.

The substrate 100 may include a microscopic element 9 that should be examined. The microscopic element 9 may be a desired part of the substrate (such as a trench, a bump and the like), an undesired part of the substrate, or a foreign particle that is connected to the substrate or placed on top of the substrate.

The microscopic element has at least one dimension (such as height, length, thickness, width, and the like) of an order of microns, sub-microns, nanometers and below.

In FIGS. 1A-1E and 2 the microscopic element 9 is illustrated as a foreign particle that is positioned on the substrate 100.

The image obtaining module 30 of system 10 may include a controller 50 and charged particles optics 40.

Charged particles optics 40 is arranged to illuminate one or more regions of the substrate 100 with an electron beam 111.

It is assumed that one of the regions includes the microscopic element 9 and a background area 102 that is proximate to the microscopic element 9 but differs from the microscopic element 9.

FIG. 1A illustrates the charged particles optics 40 as including an energy dispersive x-ray (EDX) detector 43, a secondary electron detector 42 and a backscattered electron detector 41.

It is noted that a single detector may be used for detecting secondary electrons and backscattered electrons. The single detector is biased in different manners when detecting secondary electrons and when detecting backscattered electrons.

It is noted that the charged particles optics 40 may include only the EDX detector 43 or may include the EDX detector 43 and only one of the secondary electron detector 42 and the backscattered electron detector 41.

It is noted that the charged particles optics 40 may include more than one energy dispersive x-ray detector, may include more than one secondary electron detector and/or may include more than one backscattered electron detector.

It is noted that while FIG. 1A illustrates backscattered electron detector 41, secondary electron detector 42 and EDX detector 43 as being positioned as in-lens detectors, that at least one of backscattered electron detector 41, secondary electron detector 42 and EDX detector 43 may be positioned as out-of-lens detector.

FIG. 1A illustrates a secondary electron image 130 of region 103 that is obtained by secondary electron detector 42, a backscattered electron image 120 of region 103 that was obtained by backscattered electron detector 41 and energy spectrum 140 obtained by EDX detector 43. The x-axis of the energy spectrum 140 is photon energy and the y-axis is a count.

Backscattered electron image 120, secondary electron image 130 and energy spectrum 140 may be obtained concurrently or at different points of time. The secondary electron image 130 and the backscattered electron image 120 may cover the same region 103 or different regions.

System 10 may be configured to:

a. Receive or generate an estimated composition (denoted 72 in FIG. 1A) of microscopic element 9. The estimated composition of the microscopic element is generated by analyzing the energy spectrum 140 of, at least, the microscopic element. The energy spectrum 140 is obtained by EDX detector 43. The system 10 may, for example, receive the energy spectrum and calculate the estimated composition based on the energy spectrum.

b. Receive or generate additional information (denoted 71 in FIG. 1A) related to, at least, the microscopic element. The additional information 71 is not obtained by the EDX detector 43 or by another material analysis detector. The additional information differentiates between two material of ambiguous EDX composition determination.

c. Resolve an ambiguity in the estimated composition of the microscopic element (if such an ambiguity exists) in response to the additional information. The ambiguity may occur when the energy spectrum includes a predefined energy peak that is attributed to a predefined material of ambiguous EDX composition determination. The predefined material of ambiguous EDX composition determination may belong to a group of materials of ambiguous EDX composition determination. The resolving of the ambiguity may include selecting a selected material of ambiguous EDX composition determination out of the materials of ambiguous EDX composition determination that belong to the group of materials of ambiguous EDX composition determination. The resolution of the ambiguity provides an updated estimated composition of the microscopic element.

Non-limiting examples of groups of materials of ambiguous EDX composition determination are listed in the following table (each row of the table represents a group of materials of ambiguous EDX composition determination):

| First material of ambiguous EDX composition determination | Second (or third) material of ambiguous EDX composition determination |
| --- | --- |
| Ta | Si, Rb |
| Si | Ta, W |
| W | Si |
| Ti | N |
| O | V, Cr |
| F | Fe |
| Zn | Na |

Non-limiting examples of the additional information may include at least one out of:

a. One or more secondary electron images (such as secondary electron image 130 of FIG. 1A) of a region that includes the microscopic element. The region may also include a background area—an area that is proximate to the microscopic element but is not the microscopic element. The region may only include the microscopic element or only a portion of the microscopic element.

b. A result of a process that is applied on the one or more secondary electron image.

c. One or more backscattered electron images of the region. See, for example backscattered electron image 120 of FIG. 1A.

d. A result of a process that is applied on one or more backscattered electron image.

e. One or more secondary electron images of the region and one or more backscattered electron images of the region.

f. A result of a process that is applied on the one or more secondary electron image and on the one or more backscattered electron images.

g. Coordinates of the microscopic element within an imaginary plane (such as imaginary XY plane).

h. A mapping between the coordinates of the microscopic element within the imaginary plane and an expected composition of the microscopic element.

i. A first mapping between the coordinates of the microscopic element within the imaginary plane and a height of the microscopic element.

j. A second mapping between the height of the microscopic element and an expected composition of the microscopic element.

Examples of results of a process that is applied on one or more images (one or more backscattered electron images, one or more secondary electron images or a combination of both) may be:

a. An output image that is generated by averaging multiple secondary electron images.

b. One or more attributes of one or more image.

An attribute may be, for example:

i. A contrast between pixels of the microscopic element and pixels of the background area. The contrast can be a normalized contrast or a non-normalized contrast. A normalized contrast can be calculated by dividing (a) a difference between the brightness of pixels of the microscopic element and the brightness of pixels of the background area by (b) a sum of the brightness of pixels of the microscopic element and the brightness of pixels of the background area. Heavier materials can have a higher contrast values that lighter materials.

ii. A brightness of the pixels of the microscopic element. For example—heavier materials can have a higher brightness value that lighter materials. It is noted that the pixel brightness can be normalized to the number of electrons emitted for this pixel.

iii. Assuming that the microscopic element is a defect—an attribute may be a class of the defect.

c. A comparison between one or more attributes of different images. For example—a result may be, for example, a comparison between (i) one or more attributes of one or more secondary electron images and (ii) a corresponding one or more attributes of one or more backscattered electron image.

d. A comparison can be made, for example, between (a) a contrast between pixels of the microscopic element and pixels of a background area of a backscattered electron image and (b) a contrast between pixels of the microscopic element and pixels of the background area of a secondary electron image.

One of the following formulas may be used to calculate the contrast:

$$\text{Contrast(SE)} = (I\text{defect(SE)} - I\text{background(SE)})/(I\text{defect(SE)} + I\text{background(SE)}). \quad (1)$$

Wherein Contrast(SE) is a contrast calculated from a secondary electron image, Idefect(SE) is the intensity of the pixels of the defect and Ibackground(SE) is the intensity of the pixels of the background. Both Idefect(SE) and Ibackground(SE) refer to the secondary electron image.

$$\text{Contrast(BSE)} = (I\text{defect(BSE)} - I\text{background(BSE)})/(I\text{defect(BSE)} + I\text{background(BSE)}). \quad (2)$$

Wherein Contrast(BSE) is a contrast calculated from a backscattered electron image, Idefect(BSE) is the intensity of the pixels of the defect and Ibackground(BSE) is the intensity of the pixels of the background. Both Idefect(BSE) and Ibackground(BSE) refer to the backscattered electron image.

$$\text{Contrast(SE-BSE)} = (I\text{defect(SE)} - I\text{defect(BSE)})/(I\text{defect(SE)} + I\text{defect(BSE)}). \quad (3)$$

Wherein the Contrast (SE-BSE) is a contrast calculated from a defect pixels of the secondary electron image and the backscattered electron image.

Figure 1B:
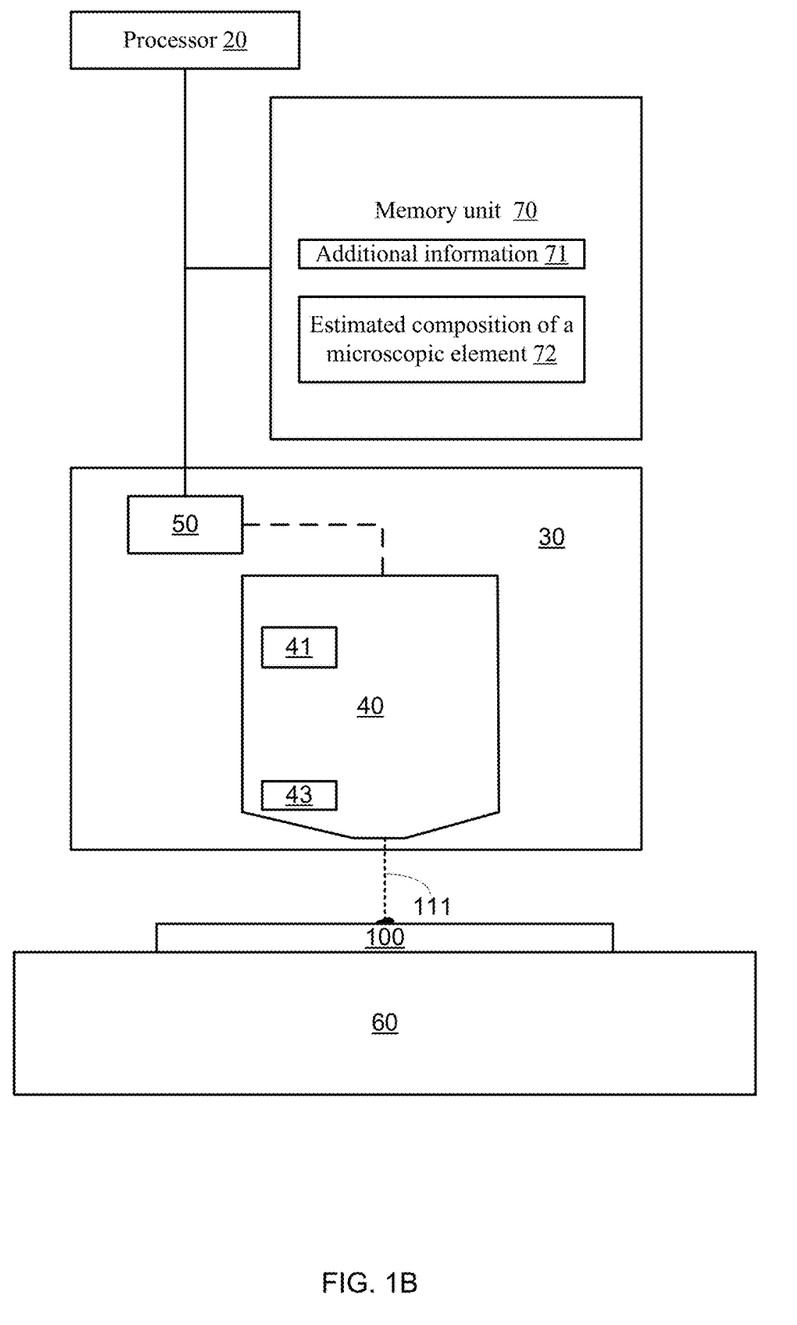
FIG. 1B illustrates a system and a substrate according to an embodiment of the disclosure.

FIG. 1B illustrates system 10 as including EDX detector 43 and backscattered electron detector 41 that are positioned as in-lens detectors.

Figure 1C:
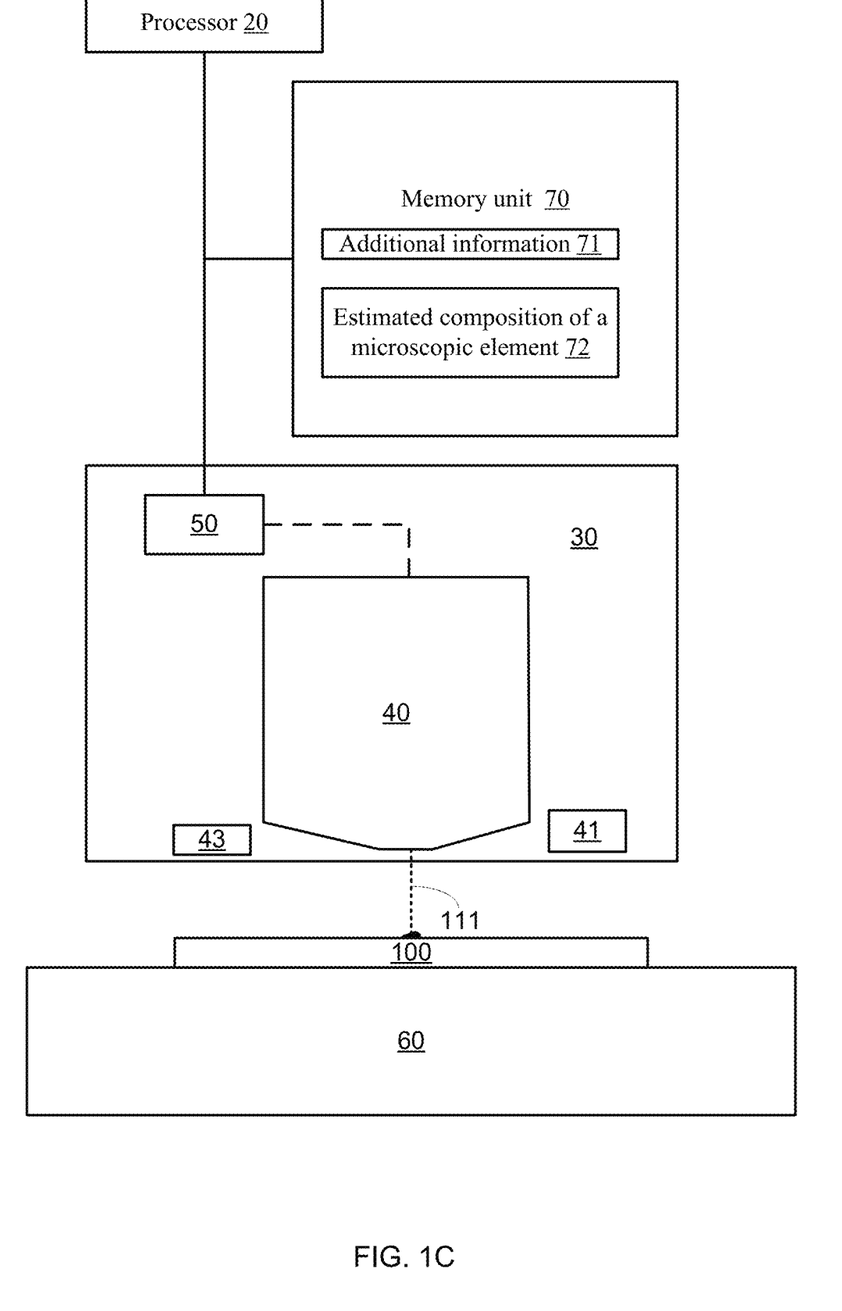
FIG. 1C illustrates a system and a substrate according to an embodiment of the disclosure.

FIG. 1C illustrates system 10 as including EDX detector 43 and backscattered electron detector 41 that are positioned as out-of-lens detectors.

Figure 1D:
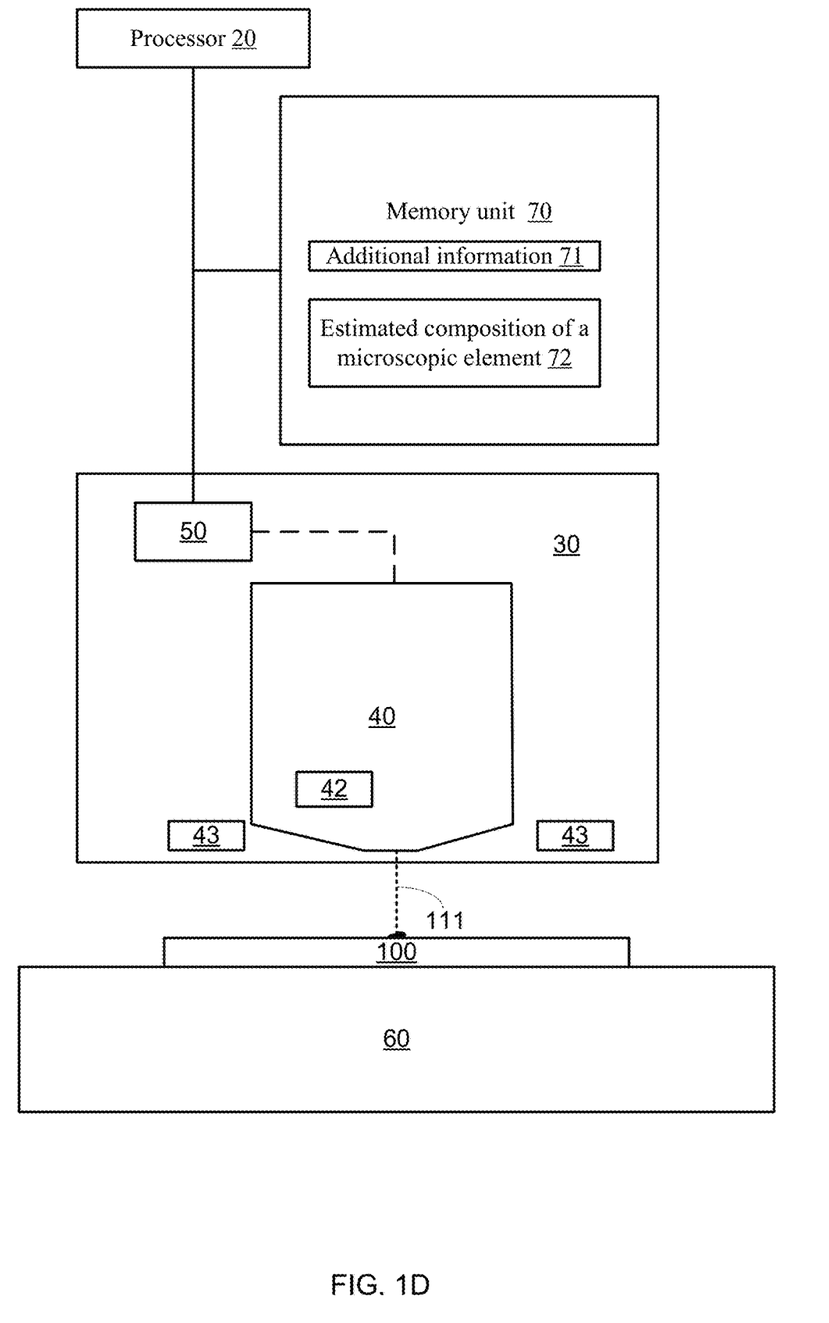
FIG. 1D illustrates a system and a substrate according to an embodiment of the disclosure.

FIG. 1D illustrates system 10 as including two EDX detectors 43 that are positioned as out-of-lens detectors and secondary electron detector 42 that is positioned as an in-lens detector.

The illumination of the region 103 with the electron beam 111 may result in an emission of secondary electrons, backscattered electrons and x-rays photons. These different electrons and/or photons may be emitted simultaneously or at different periods of time—for example when the charged particle optics 40 is tuned to different modes of operation.

Figure 1E:
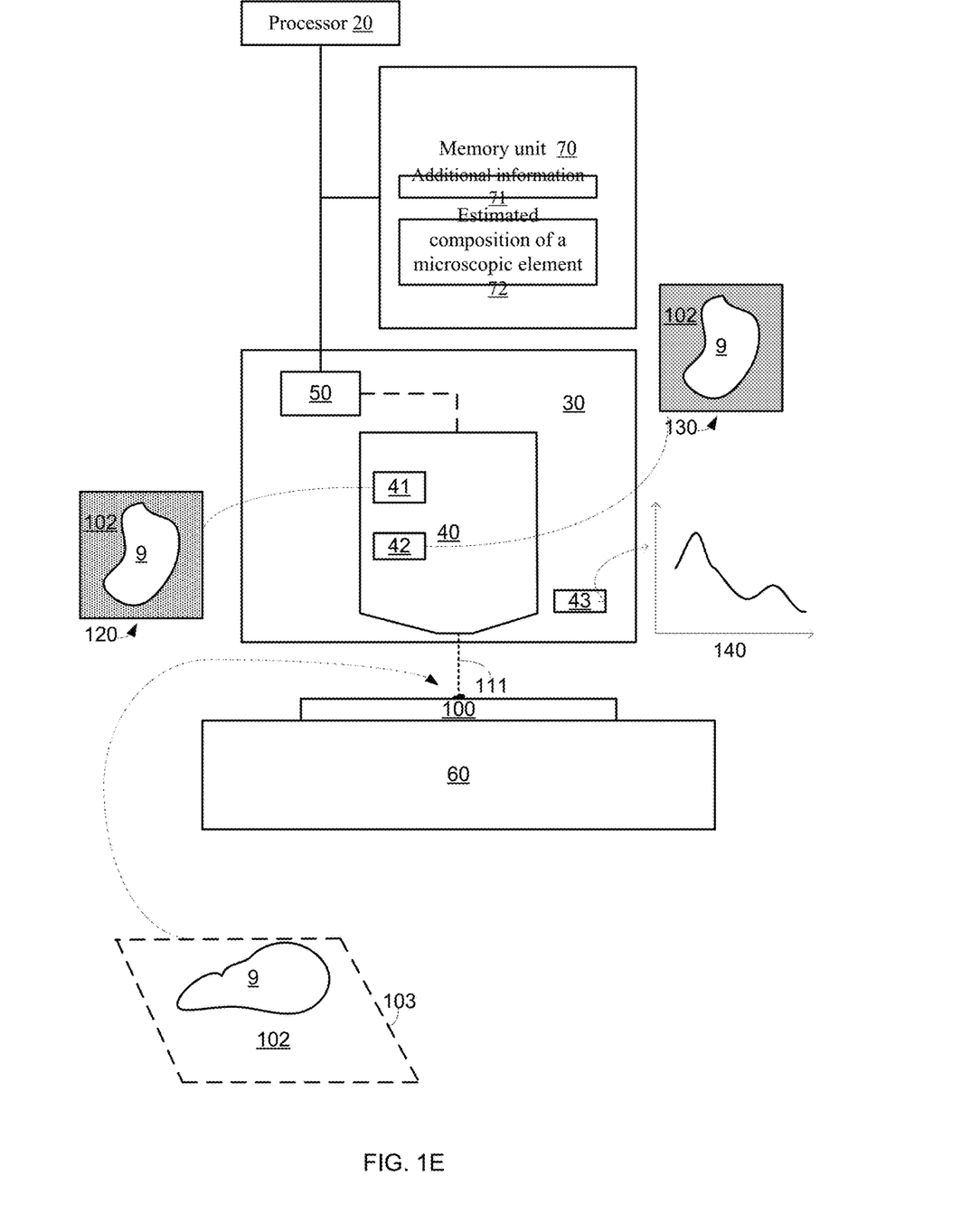
FIG. 1E illustrates a system and a substrate according to an embodiment of the disclosure.

FIG. 1E illustrates system 10 as including an out-of-lens EDX detector 43 as well as secondary electron detector 42 and backscattered electron detector 41 that are positioned as in-lens detectors.

Figure 2:
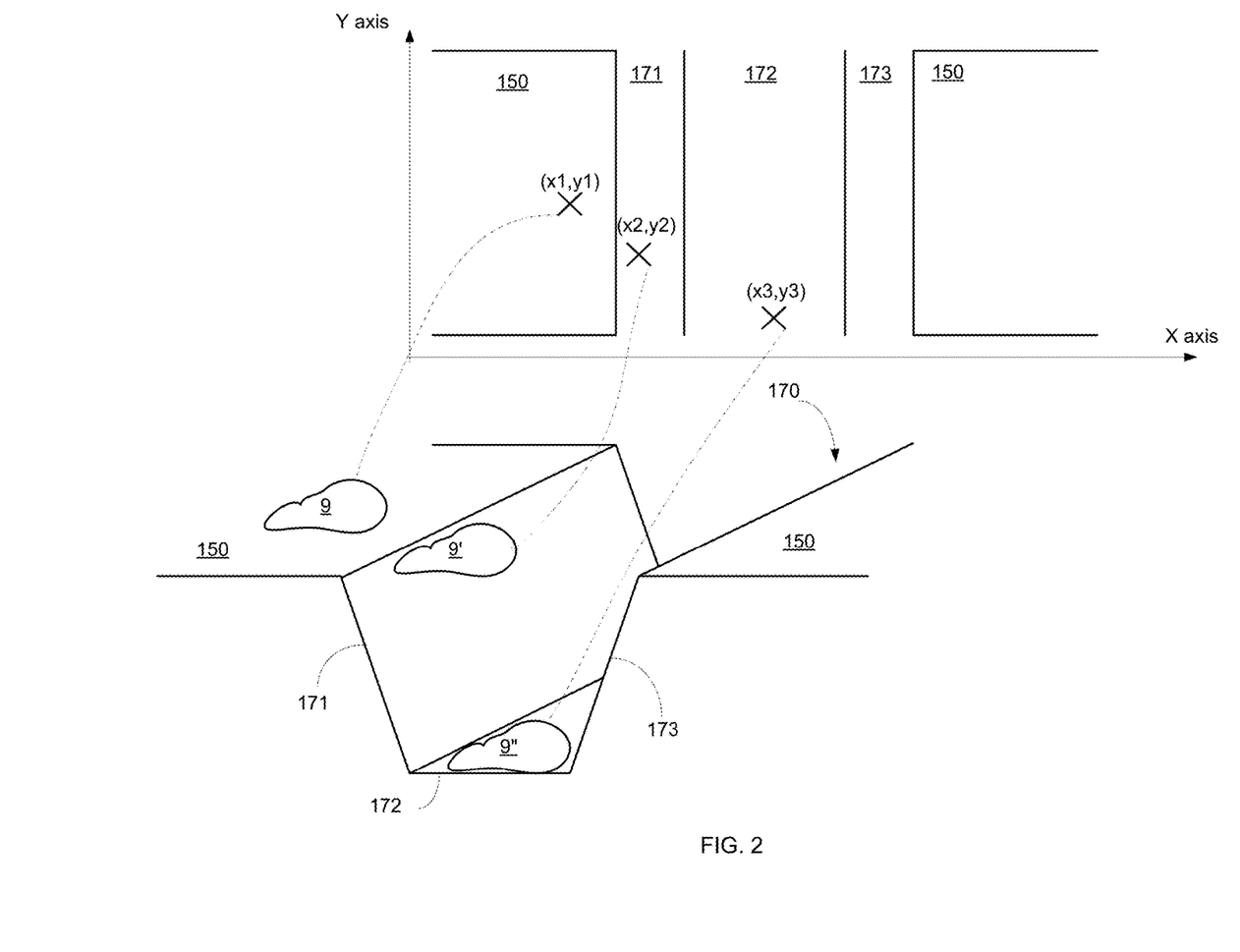
FIG. 2 illustrates a microscopic trench, multiple defects and a mapping according to an embodiment of the disclosure.

FIG. 2 includes a top view and an isometric view of three microscopic elements 9, 9' and 9" and a trench 170 according to an embodiment of the disclosure.

Trench 170 includes left sidewall 171, bottom 172 and right sidewall 173. Trench 170 is surrounded by surface 150.

The relationship (first mapping) between each XY coordinate of the trench 170 and surface and the height of said coordinates is known (or estimated). The height of microscopic element 9 can be driven from the XY coordinates (x1,y1) of microscopic element 9. The height of microscopic element 9' can be driven from the XY coordinates (x2,y2) of microscopic element 9'. The height of microscopic element 9" can be driven from the XY coordinates (x3,y3) of microscopic element 9".

Figure 3:
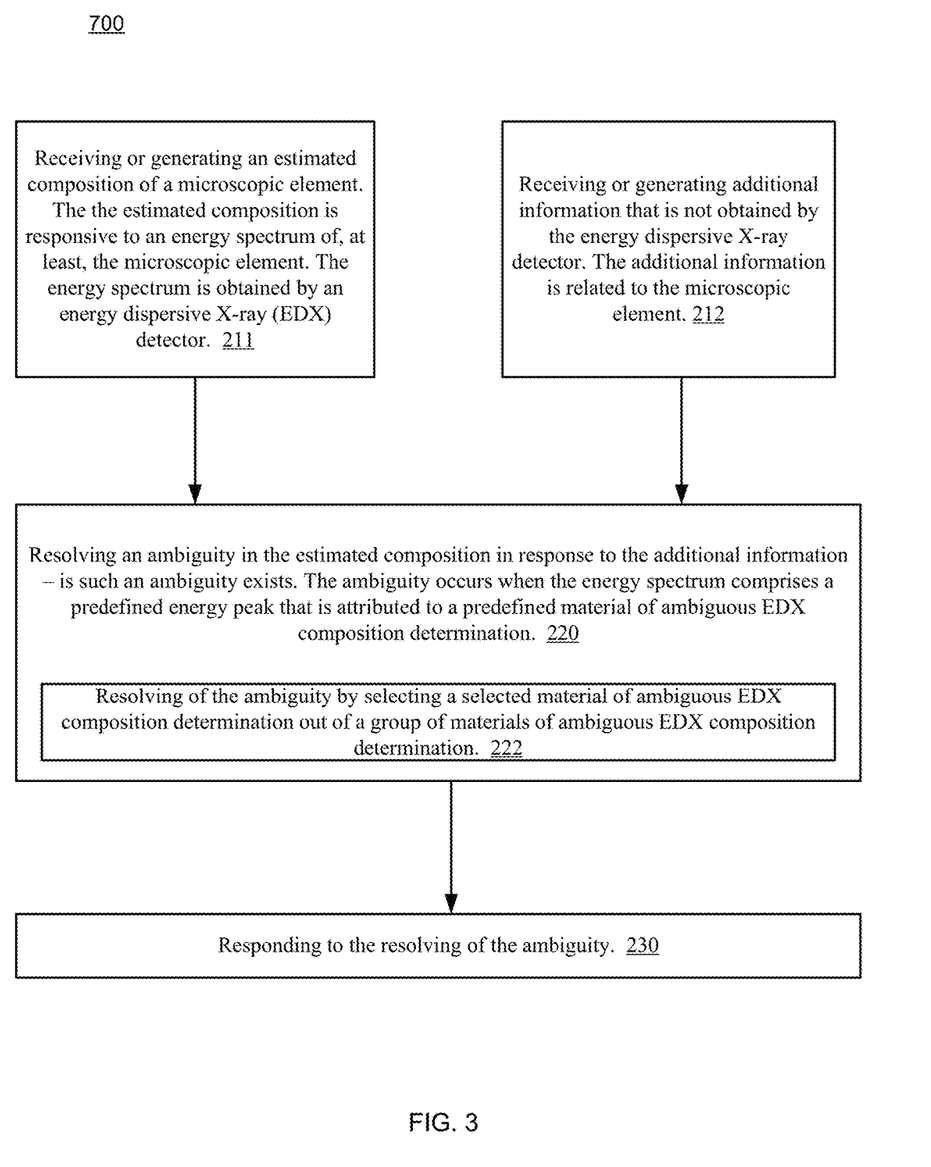
FIG. 3 illustrates a method according to an embodiment of the disclosure.

FIG. 3 illustrates method 200 according to an embodiment of the disclosure.

Method 200 may start by steps 211 and 212.

Step 211 may include receiving or generating an estimated composition of a microscopic element. The estimated composition is responsive to an energy spectrum of, at least, the microscopic element. The energy spectrum is obtained by an energy dispersive X-ray detector.

Step 212 may include receiving or generating additional information that is not obtained by the energy dispersive X-ray detector. The additional information is related to the microscopic element.

Steps 211 and 212 may be followed by step 220 of resolving an ambiguity in the estimated composition in response to the additional information—is such an ambiguity exists. The ambiguity occurs when the energy spectrum includes a predefined energy peak that is attributed to a predefined material of ambiguous EDX composition determination.

The resolving of the ambiguity includes providing an updated estimated composition of the microscopic element.

The predefined material of ambiguous EDX composition determination may belong to a group of materials of ambiguous EDX composition determination. Step 220 may include step 222 of resolving of the ambiguity by selecting a selected material of ambiguous EDX composition determination out of the materials of ambiguous EDX composition determination that belong to the group of materials of ambiguous EDX composition determination.

The additional information may be indicative of an expected composition of the microscopic element. Step 222 may include selecting of the selected material of ambiguous EDX composition determination in response to the expected composition of the microscopic element.

The microscopic element may be a defect. The additional information may be indicative of a class of the defect. Step 222 may include selecting of the selected material of ambiguous EDX composition determination in response to the class of the defect.

The additional information may include (a) coordinates of the microscopic element within an imaginary plane, and (b) a mapping between the coordinates of the microscopic element within the imaginary plane and an expected composition of the microscopic element. Step 222 may include selecting of the selected material of ambiguous EDX composition determination in response to the mapping and to the coordinates of the microscopic element within the imaginary plane.

The additional information may include (i) coordinates of the microscopic element within an imaginary plane, (ii) a first mapping between the coordinates of the microscopic element within the imaginary plane and a height of the microscopic element, and (ii) a second mapping between the height of the microscopic element and an expected composition of the microscopic element. Step 222 may include selecting of the selected material of ambiguous EDX composition determination in response to the first mapping, to the second mapping and to the coordinates of the microscopic element within the imaginary plane.

The additional information may be design information indicative of locations of different layers of a substrate and of compositions of the different layers of the substrate. The microscopic element may be either included in the substrate is located above the substrate. Step 222 may include selecting of the selected material of ambiguous EDX composition determination in response to the design information.

Step 220 may be followed by step 230 of responding to the resolving of the ambiguity in the estimated composition.

Step 230 may include, for example, displaying and/or storing and/or transmitting a corrected x-ray spectrum.

Step 230 may include, for example, using the corrected spectrum in order to feed further analysis step, for example automatic defect composition determination.

The disclosure may also be implemented in a computer program for running on a computer system, at least including code portions for performing steps of a method according to the disclosure when run on a programmable apparatus, such as a computer system or enabling a programmable apparatus to perform functions of a device or system according to the disclosure. The computer program may cause the storage system to allocate disk drives to disk drive groups.

A computer program is a list of instructions such as a particular application program and/or an operating system. The computer program may for instance include one or more of: a subroutine, a function, a procedure, a method, an object implementation, an executable application, an applet, a servlet, a source code, an object code, a shared library/dynamic load library and/or other sequence of instructions designed for execution on a computer system.

The computer program may be stored internally on a non-transitory computer readable medium. All or some of the computer program may be provided on computer readable media permanently, removable or remotely coupled to an information processing system. The computer readable media may include, for example and without limitation, any number of the following: magnetic storage media including disk and tape storage media; optical storage media such as compact disk media (e.g., CD-ROM, CD-R, etc.) and digital video disk storage media; nonvolatile memory storage media including semiconductor-based memory units such as flash memory, EEPROM, EPROM, ROM; ferromagnetic digital memories; MRAM; volatile storage media including registers, buffers or caches, main memory, RAM, etc.

A computer process typically includes an executing (running) program or portion of a program, current program values and state information, and the resources used by the operating system to manage the execution of the process. An operating system (OS) is the software that manages the sharing of the resources of a computer and provides programmers with an interface used to access those resources. An operating system processes system data and user input, and responds by allocating and managing tasks and internal system resources as a service to users and programs of the system.

The computer system may for instance include at least one processing unit, associated memory and a number of input/output (I/O) devices. When executing the computer program, the computer system processes information according to the computer program and produces resultant output information via I/O devices.

In the foregoing specification, the disclosure has been described with reference to specific examples of embodiments of the disclosure. It will, however, be evident that various modifications and changes may be made therein without departing from the broader spirit and scope of the disclosure as set forth in the appended claims.

Moreover, the terms "front," "back," "top," "bottom," "over," "under" and the like in the description and in the claims, if any, are used for descriptive purposes and not necessarily for describing permanent relative positions. It is understood that the terms so used are interchangeable under appropriate circumstances such that the embodiments of the disclosure described herein are, for example, capable of operation in other orientations than those illustrated or otherwise described herein.

The connections as discussed herein may be any type of connection suitable to transfer signals from or to the respective nodes, units or devices, for example via intermediate devices. Accordingly, unless implied or stated otherwise, the connections may for example be direct connections or indirect connections. The connections may be illustrated or described in reference to being a single connection, a plurality of connections, unidirectional connections, or bidirectional connections. However, different embodiments may vary the implementation of the connections. For example, separate unidirectional connections may be used rather than bidirectional connections and vice versa. Also, plurality of connections may be replaced with a single connection that transfers multiple signals serially or in a time multiplexed manner. Likewise, single connections carrying multiple signals may be separated out into various different connections carrying subsets of these signals. Therefore, many options exist for transferring signals.

Although specific conductivity types or polarity of potentials have been described in the examples, it will be appreciated that conductivity types and polarities of potentials may be reversed.

Each signal described herein may be designed as positive or negative logic. In the case of a negative logic signal, the signal is active low where the logically true state corresponds to a logic level zero. In the case of a positive logic signal, the signal is active high where the logically true state corresponds to a logic level one. Note that any of the signals described herein may be designed as either negative or positive logic signals. Therefore, in alternate embodiments, those signals described as positive logic signals may be implemented as negative logic signals, and those signals described as negative logic signals may be implemented as positive logic signals.

Furthermore, the terms "assert" or "set" and "negate" (or "deassert" or "clear") are used herein when referring to the rendering of a signal, status bit, or similar apparatus into its logically true or logically false state, respectively. If the logically true state is a logic level one, the logically false state is a logic level zero. And if the logically true state is a logic level zero, the logically false state is a logic level one.

Those skilled in the art will recognize that the boundaries between logic blocks are merely illustrative and that alternative embodiments may merge logic blocks or circuit elements or impose an alternate decomposition of functionality upon various logic blocks or circuit elements. Thus, it is to be understood that the architectures depicted herein are merely exemplary, and that in fact many other architectures may be implemented which achieve the same functionality.

Any arrangement of components to achieve the same functionality is effectively "associated" such that the desired functionality is achieved. Hence, any two components herein combined to achieve a particular functionality may be seen as "associated with" each other such that the desired functionality is achieved, irrespective of architectures or intermedial components. Likewise, any two components so associated can also be viewed as being "operably connected," or "operably coupled," to each other to achieve the desired functionality.

Furthermore, those skilled in the art will recognize that boundaries between the above described operations merely illustrative. The multiple operations may be combined into a single operation, a single operation may be distributed in additional operations and operations may be executed at least partially overlapping in time. Moreover, alternative embodiments may include multiple instances of a particular operation, and the order of operations may be altered in various other embodiments.

Also for example, in one embodiment, the illustrated examples may be implemented as circuitry located on a single integrated circuit or within a same device. Alternatively, the examples may be implemented as any number of separate integrated circuits or separate devices interconnected with each other in a suitable manner.

Also for example, the examples, or portions thereof, may implemented as soft or code representations of physical circuitry or of logical representations convertible into physical circuitry, such as in a hardware description language of any appropriate type.

Also, the disclosure is not limited to physical devices or units implemented in non-programmable hardware but can also be applied in programmable devices or units able to perform the desired device functions by operating in accordance with suitable program code, such as mainframes, minicomputers, servers, workstations, personal computers, notepads, personal digital assistants, electronic games, automotive and other embedded systems, cell phones and various other wireless devices, commonly denoted in this application as 'computer systems'.

However, other modifications, variations and alternatives are also possible. The specifications and drawings are, accordingly, to be regarded in an illustrative rather than in a restrictive sense.

In the claims, any reference signs placed between parentheses shall not be construed as limiting the claim. The word 'comprising' does not exclude the presence of other elements or steps then those listed in a claim. Furthermore, the terms "a" or "an," as used herein, are defined as one or more than one. Also, the use of introductory phrases such as "at least one" and "one or more" in the claims should not be construed to imply that the introduction of another claim element by the indefinite articles "a" or "an" limits any particular claim containing such introduced claim element to disclosures containing only one such element, even when the same claim includes the introductory phrases "one or more" or "at least one" and indefinite articles such as "a" or "an." The same holds true for the use of definite articles. Unless stated otherwise, terms such as "first" and "second" are used to arbitrarily distinguish between the elements such terms describe. Thus, these terms are not necessarily intended to indicate temporal or other prioritization of such elements. The mere fact that certain measures are recited in mutually different claims does not indicate that a combination of these measures cannot be used to advantage.

While certain features of the disclosure have been illustrated and described herein, many modifications, substitutions, changes, and equivalents will now occur to those of ordinary skill in the art. It is, therefore, to be understood that the appended claims are intended to cover all such modifications and changes as fall within the true spirit of the disclosure.

We claim:

1. A system, comprising a processor configured to:
   receive or generate:
   (i) an estimated composition of a microscopic element; wherein the estimated composition is responsive to an energy spectrum of, at least, the microscopic element; wherein the energy spectrum is obtained by an energy dispersive X-ray (EDX) detector; and
   (ii) additional information related to, at least, the microscopic element, wherein the additional information includes at least one of a backscattered electron image or a secondary electron image of a region including the microscopic element; and
   resolve an ambiguity in the estimated composition in response to the additional information, wherein the ambiguity occurs when the energy spectrum comprises a predefined energy peak that is attributed to a predefined material of ambiguous EDX composition determination from a group of materials of ambiguous EDX composition determination, and wherein resolving the ambiguity in the estimated composition in response to the additional information includes selecting the predefined material of ambiguous EDX composition determination out of the group of materials of ambiguous EDX composition determination based on:
   (i) a brightness of the microscopic element and a brightness of a background area of the region in the backscattered electron image or the secondary electron image;
   (ii) coordinates of the microscopic element within an imaginary plane determined based on the backscattered electron image or the secondary electron image, and a mapping between the coordinates of the microscopic element within the imaginary plane and an expected composition of the microscopic element; or
   (iii) coordinates of the microscopic element within an imaginary plane determined based on the backscattered electron image or the secondary electron image, a first mapping between the coordinates of the microscopic element within the imaginary plane and a height of the microscopic element, and a second mapping between the height of the microscopic element and an expected composition of the microscopic element.

2. The system according to claim 1 wherein the backscattered electron image or the secondary electron image is obtained concurrently with the energy spectrum obtained by the energy dispersive X-ray detector.

3. The system according to claim 1 wherein a heavier material of the group of materials of ambiguous EDX composition determination has a higher contrast between the brightness of the microscopic element and the brightness of the background area of the region in the backscattered electron image or the secondary electron image than a lighter material.

4. The system according to claim 1 wherein a heavier material of the group of materials of ambiguous EDX composition determination has a higher brightness in the backscattered electron image or the secondary electron image than a lighter material.

5. A method for material analysis, the method comprising:
  (a) receiving or generating: (i) an estimated composition of a microscopic element; wherein the estimated composition is responsive to an energy spectrum of, at least, the microscopic element; wherein the energy spectrum is obtained by an energy dispersive X-ray (EDX) detector; and (ii) additional information related to, at least, the microscopic element, wherein the additional information includes at least one of a backscattered electron image or a secondary electron image of a region including the microscopic element; and
  (b) resolving an ambiguity in the estimated composition in response to the additional information, wherein the ambiguity occurs when the energy spectrum comprises a predefined energy peak that is attributed to a predefined material of ambiguous EDX composition determination from a group of materials of ambiguous EDX composition determination, and wherein resolving the ambiguity in the estimated composition in response to the additional information includes selecting the predefined material of ambiguous EDX composition determination out of the group of materials of ambiguous EDX composition determination based on:
    (i) a brightness of the microscopic element and a brightness of a background area of the region in the backscattered electron image or the secondary electron image;
    (ii) coordinates of the microscopic element within an imaginary plane determined based on the backscattered electron image or the secondary electron image, and a mapping between the coordinates of the microscopic element within the imaginary plane and an expected composition of the microscopic element; or
    (iii) coordinates of the microscopic element within an imaginary plane determined based on the backscattered electron image or the secondary electron image, a first mapping between the coordinates of the microscopic element within the imaginary plane and a height of the microscopic element, and a second mapping between the height of the microscopic element and an expected composition of the microscopic element.

6. The method according to claim 5 wherein the microscopic element includes a defect and wherein the additional information further includes an indication of a class of the defect, wherein the selecting of the predefined material of ambiguous EDX composition determination is based on the class of the defect.

7. The method according to claim 5 wherein the additional information further includes design information indicative of locations of different layers of a substrate and of compositions of the different layers of the substrate; wherein the microscopic element is either included in the substrate or located above the substrate.

8. The method according to claim 5 wherein the additional information is obtained by processing at least one secondary electron image of the region that comprises the microscopic element.

9. The method according to claim 5 wherein the additional information is obtained by processing at least one backscattered electron image of the region that comprises the microscopic element.

10. The method according to claim 5 wherein the additional information is obtained by processing at least one backscattered electron image and at least one secondary electron image of the region that comprises the microscopic element.

11. The method according to claim 5 wherein the additional information is obtained by comparing between (a) an attribute of the backscattered electron image of the region that comprises the microscopic element; and (b) an attribute of the secondary electron image of the region.

12. The method according to claim 11 wherein the attribute of the secondary electron image is a relationship between pixels of the microscopic element and pixels of a background area of the region.

13. The method according to claim 12 wherein the relationship is a contrast between the pixels of the microscopic element and the pixels of the background area.

14. The method according to claim 5 wherein the backscattered electron image or the secondary electron image is obtained concurrently with the energy spectrum obtained by the energy dispersive X-ray detector.

15. The method according to claim 5 wherein a heavier material of the group of materials of ambiguous EDX composition determination has a higher contrast between the brightness of the microscopic element and the brightness of the background area of the region in the backscattered electron image or the secondary electron image than a lighter material.

16. The method according to claim 5 wherein a heavier material of the group of materials of ambiguous EDX composition determination has a higher brightness in the backscattered electron image or the secondary electron image than a lighter material.

17. A non-transitory computer readable medium that stores instructions that once executed by a computer cause the computer to:
  receive or generate (i) an estimated composition of a microscopic element; wherein the estimated composition is responsive to an energy spectrum of, at least, the microscopic element; wherein the energy spectrum is obtained by an energy dispersive X-ray (EDX) detector; and (ii) additional information related to, at least, the microscopic element, wherein the additional information includes at least one of a backscattered electron image or a secondary electron image of a region including the microscopic element; and
  resolve an ambiguity in the estimated composition in response to the additional information, wherein the ambiguity occurs when the energy spectrum comprises a predefined energy peak that is attributed to a predefined material of ambiguous EDX composition determination from a group of materials of ambiguous EDX composition determination, and wherein resolving the ambiguity in the estimated composition in response to the additional information includes selecting the predefined material of ambiguous EDX composition determination out of the group of materials of ambiguous EDX composition determination based on:
(i) a brightness of the microscopic element and a brightness of a background area of the region in the backscattered electron image or the secondary electron image;
(ii) coordinates of the microscopic element within an imaginary plane determined based on the backscattered electron image or the secondary electron image, and a mapping between the coordinates of the microscopic element within the imaginary plane and an expected composition of the microscopic element; or
(iii) coordinates of the microscopic element within an imaginary plane determined based on the backscattered electron image or the secondary electron image, a first mapping between the coordinates of the microscopic element within the imaginary plane and a height of the microscopic element, and a second mapping between the height of the microscopic element and an expected composition of the microscopic element.

18. The non-transitory computer readable medium according to claim 17 wherein the backscattered electron image or the secondary electron image is obtained concurrently with the energy spectrum obtained by the energy dispersive X-ray detector.

19. The non-transitory computer readable medium according to claim 17 wherein a heavier material of the group of materials of ambiguous EDX composition determination has a higher contrast between the brightness of the microscopic element and the brightness of the background area of the region in the backscattered electron image or the secondary electron image than a lighter material.

20. The non-transitory computer readable medium according to claim 17 wherein a heavier material of the group of materials of ambiguous EDX composition determination has a higher brightness in the backscattered electron image or the secondary electron image than a lighter material.

* * * * *